United States Patent
Royce

(10) Patent No.: US 12,039,824 B2
(45) Date of Patent: Jul. 16, 2024

(54) MODULAR PRESCRIPTION FILLING SYSTEM AND FACILITIES

(71) Applicant: Innovation Associates, Inc., Johnson City, NY (US)

(72) Inventor: David Royce, Johnson City, NY (US)

(73) Assignee: Innovation Associates, Inc., Johnson City, NY (US)

(*) Notice: Subject to any disclaimer, the term of this patent is extended or adjusted under 35 U.S.C. 154(b) by 144 days.

(21) Appl. No.: 17/494,331

(22) Filed: Oct. 5, 2021

(65) Prior Publication Data

US 2022/0114855 A1 Apr. 14, 2022

Related U.S. Application Data

(60) Provisional application No. 63/089,318, filed on Oct. 8, 2020.

(51) Int. Cl.
  *G07F 17/00* (2006.01)
  *G16H 20/10* (2018.01)

(52) U.S. Cl.
  CPC ......... *G07F 17/0092* (2013.01); *G16H 20/10* (2018.01)

(58) Field of Classification Search
  CPC ..... G07F 17/0092; G16H 20/13; B65B 3/003; B65B 5/103; B65B 1/04
  See application file for complete search history.

(56) References Cited

U.S. PATENT DOCUMENTS

| | | | | |
|---|---|---|---|---|
| 5,277,534 A * | 1/1994 | Anderson | ............... | B65G 1/045 414/280 |
| 6,006,946 A * | 12/1999 | Williams | ............ | G07F 17/0092 221/9 |
| 6,788,997 B1 * | 9/2004 | Frederick | ............ | G07F 17/0092 312/351 |
| 8,060,248 B1 * | 11/2011 | Boyer | ..................... | B65B 57/20 700/235 |
| 8,342,400 B1 * | 1/2013 | Reese | .................... | G16H 20/13 340/568.1 |
| 11,273,103 B1 * | 3/2022 | Brakkee | ............... | G07F 17/0092 |
| 2003/0085235 A1 * | 5/2003 | William | .................. | G16H 20/13 221/92 |
| 2006/0259195 A1 * | 11/2006 | Eliuk | ................... | G07F 17/0092 700/245 |
| 2011/0017764 A1 * | 1/2011 | Liguori | ............... | G07F 11/1657 221/1 |
| 2016/0200462 A1 * | 7/2016 | Kriheli | ................ | G07F 17/0092 700/214 |
| 2018/0082757 A1 * | 3/2018 | Chambers | ........... | G07F 17/0092 |

* cited by examiner

*Primary Examiner* — Timothy R Waggoner
(74) *Attorney, Agent, or Firm* — K&L Gates LLP

(57) ABSTRACT

Methods and systems for providing improved prescription filling systems are disclosed. In one embodiment, a prescription filling system is provided that includes a primary module and at least one expansion module. The primary module may include shelves that each contains a plurality of equipment brackets. The primary module may also include a supplementary system positioned between the shelves. The at least one expansion module may also include shelves that each contain a plurality of equipment brackets. Furthermore, the primary module may contain a robotic arm that is substantially equidistant from each of the shelves within the primary module and the at least one expansion module.

19 Claims, 6 Drawing Sheets

MODULAR PRESCRIPTION FILLING SYSTEM AND FACILITIES

PRIORITY CLAIM

This application claims priority to and the benefit of U.S. Provisional Patent Application Ser. No. 63/089,318, filed on Oct. 8, 2020, the entire disclosure of which is hereby incorporated by reference.

BACKGROUND

Automated pharmacy systems are used to prepare and fill prescriptions for individuals. For example, automated machines may be used to dispense particular quantities of different types of pills or other prescriptions. Additionally, automated systems may be used to collect counted pills in containers, to label the containers (e.g., with patient information, prescription information), and/or to close the containers (e.g., by fastening caps to the containers).

SUMMARY

The present disclosure presents new and innovative systems and methods for providing improved prescription filling systems. In a first aspect, a system is provided that includes a primary module and at least one expansion module. The primary module may include a first shelf containing a first plurality of equipment brackets and a second shelf containing a second plurality of equipment brackets. The primary module may also include a supplementary system positioned between the first shelf and the second shelf. The primary module may further include a robotic arm. The at least one expansion module may include a third shelf containing a third plurality of equipment brackets and a fourth shelf containing a fourth plurality of equipment brackets. The robotic arm may be substantially equidistant from each of the first shelf, the second shelf, the third shelf, and the fourth shelf.

In a second aspect, a method of assembling a prescription filling system is provided, comprising providing a primary module, providing at least one expansion module, and attaching the at least one expansion module to the primary module. The primary module may include a first shelf containing a first plurality of equipment brackets and a second shelf containing a second plurality of equipment brackets. The primary module may also include a supplementary system positioned between the first shelf and the second shelf. The primary module may further include a robotic arm. The at least one expansion module may include a third shelf containing a third plurality of equipment brackets and a fourth shelf containing a fourth plurality of equipment brackets. The robotic arm may be substantially equidistant from each of the first shelf, the second shelf, the third shelf, and the fourth shelf.

The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the disclosed subject matter.

DETAILED DESCRIPTION OF EXAMPLE EMBODIMENTS

Different prescription filling facilities may fulfill different quantities of prescription requests, or may fulfill prescription requests for different amounts of discrete types of prescription drugs. Accordingly, different prescription filling systems are typically provided in various sizes that include equipment designed to meet these requirements. For example, smaller prescription filling systems are used to fulfill smaller numbers of prescription requests, which typically experience a smaller number of discrete types of prescription drugs. These smaller prescripti0on filling systems may include fewer pill counting machines and may be smaller in size. As another example, larger prescription filling systems are designed for a larger number of prescription requests or to fulfill prescription requests for a larger number of discrete types of prescription drugs. The larger prescription filing systems may include a large number of pill counting machines and may accordingly be larger in size. However, these prescription filling systems are typically created as self-contained, all-encompassing systems. Accordingly, as a particular user's prescription filling needs grow over time (e.g., as a business expands), users may be required to purchase additional machines that replace smaller machines. Such systems can be wasteful, as smaller machines go unused or as customers are required to repurchase certain redundant components between the various machines. Accordingly, there exists a need for a prescription filling system that can be expanded easily as users' capacity grows.

Figure 1:
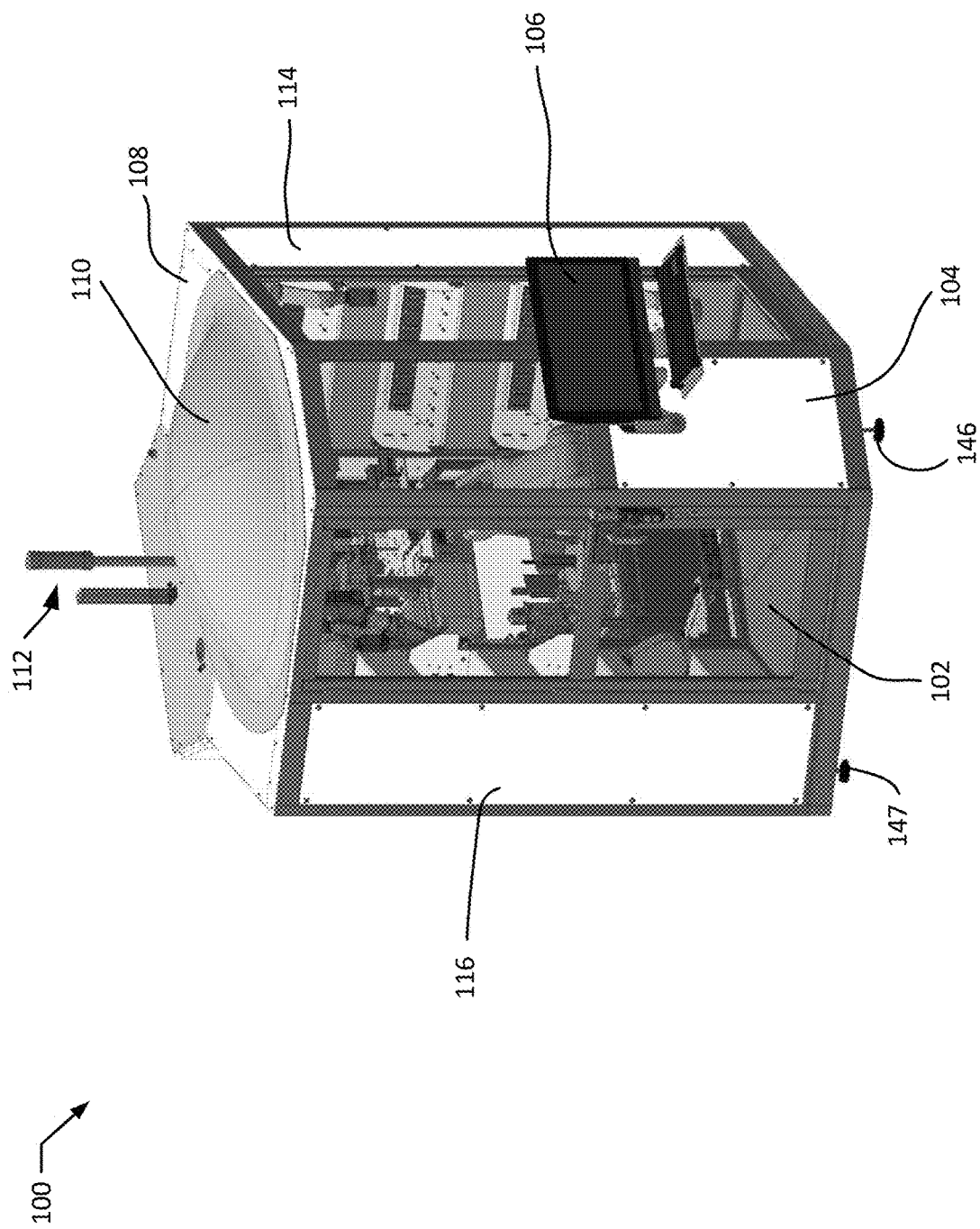
FIG. 1 illustrates an exterior view of a prescription filling system in a compact configuration, according to an exemplary embodiment of the present disclosure.

FIG. 1 illustrates an exterior view of a prescription filling system 100 in a compact configuration, according to an exemplary embodiment of the present disclosure. The prescription filling system 100 includes several exterior wall portions 114, 116. The exterior wall portions may be opaque, such as the wall portions 114, 116 and/or may be transparent, such as the wall portion 115. Additionally, the prescription filling system 100 may include a wall portion 104 that is partially opaque and partially transparent. As explained further below, the exterior wall portions of the prescription filling system 100 may be formed as part of an octagonal shape surrounding a center point. When configured in this way, the prescription filling system 100 may be expandable to include additional exterior wall sections, and may thereby be expandable to contain additional equipment, as explained further below.

In certain instances, the wall portions 104, 114, 115, 116 may store other equipment used by the prescription filling system 100. For example, the prescription filling system 100 includes a computer terminal 106, which may be configured to control or monitor prescription filling operations performed by the prescription filling system 100. For example, the computer terminal may contain a processor and a memory configured to execute software to monitor or control prescription filling operations. For example, as discussed further below, the prescription filling system 100 may include a robotic arm 142 configured to automatically fill particular prescriptions. The computer terminal 106 may be configured to display operating information for the robotic arm 142 and/or to monitor the progress of prescriptions (e.g., a queue of prescriptions for fulfillment) that are fulfilled by the prescription filling system 100 and/or the robotic arm 142. Additionally or alternatively, the computer terminal 106 may be used to add or alter prescriptions for fulfillment by the robotic arm 142.

The prescription filling system 100 also includes a roof 108 that includes a convex partition 110. The roof 108, coupled with the wall portions 104, 114 115, 116, may form a sealed environment within the prescription filling system 100. The sealed environment may prevent contaminants from entering the prescription filling system 100, reducing the contamination of prescriptions fulfilled by the prescription filling system 100. Additionally or alternatively, the sealed environment may prevent dust or other byproducts of prescription filling processes from exiting the prescription filling system 100. To maintain such a sealed environment, the prescription filling system 112 may also include ventilation systems 112, which may filter air that enters the prescription filling system 100 and air that leaves the prescription filling system 100 to prevent contaminants from entering the prescription filling system 100 and/or to prevent byproducts from leaving the prescription filling system 100. The convex portion 110 of the roof 108 may be shaped to improve maneuverability of the robotic arm 142 within the prescription filling system 100. For example, the convex portion 110 may be shaped to provide sufficient vertical height within the prescription filling system 100 to enable the robotic arm 142 to fully extend vertically when in operation. Additionally or alternatively, the convex partition 110 may provide sufficient height (e.g., 6 feet or more) to enable an individual to comfortably stand within the prescription filling system 100.

The prescription filling system 100 also includes a door 102, which may be used to enter the prescription filling system 100. For example, an individual may enter the prescription filling system 100 by the door 102 to interact with one or more components or portions of the prescription filling system 100. For example, the individual may interact with the robotic arm 142, may interact with one or more pill dispensing machines (e.g., for maintenance or resupply), may interact with one or more capping machines (e.g., for maintenance, to switch cap types), and/or may interact with other machines within the prescription filling system 100 (e.g., for maintenance or configuration). In certain instances, the door 102 may be configured to ensure that prescription filling operations are ceased by the prescription filling system 100 before the door 102 will open. For example, the door 102 may be communicatively coupled to a kill switch for the robotic arm 142 and/or other machines or components of the prescription filling system 100. Upon opening the door 102 (or requesting that the door 102 be opened or unlocked), power may be cut to the robotic arm 142 and/or operations may cease for the robotic arm 142 and other moving mechanical systems of the prescription filling system 100.

Figure 2:
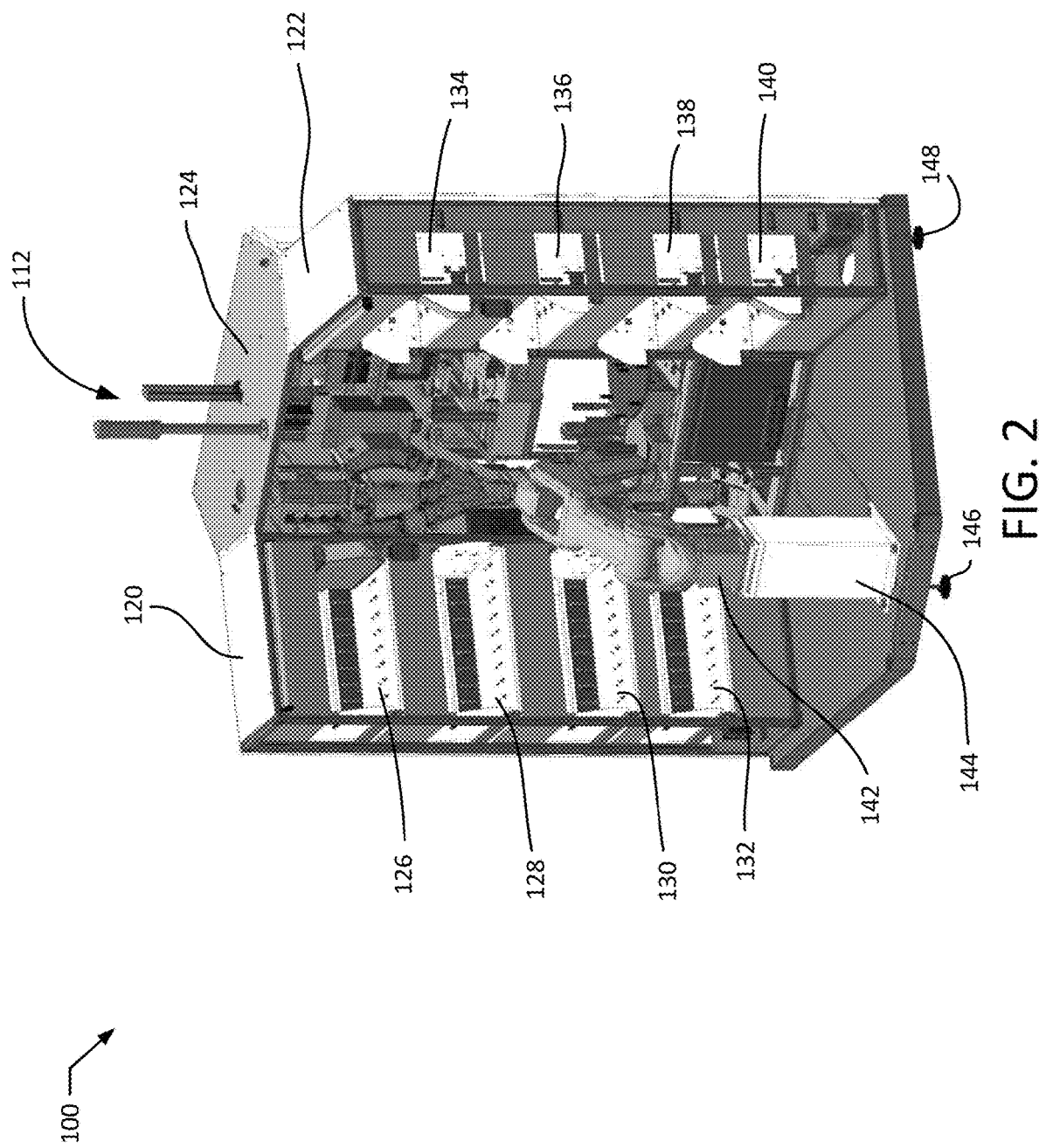
FIG. 2 illustrates an interior view of a prescription filling system in a compact configuration, according to an exemplary embodiment of the present disclosure.

Turning to FIG. 2, the interior of the prescription filling system 100 includes shelves 120, 122 and a supplementary system 124. The shelves 120, 122 include equipment brackets 126, 128, 130, 132, 134, 136, 138, 140. The equipment brackets 126, 128, 130, 132, 134, 136, 138, 140 may be configured to hold one or more machines or subsystems used by the prescription filling system. For example, the equipment brackets 126, 128, 130, 132, 134, 136, 138, 140 may be configured to securely attach to and hold in place particular types of machinery. The equipment brackets 126, 128, 130, 132, 134, 136, 138, 140 may be configured to securely hold machines of a particular size. For example, although not depicted, the equipment brackets 126, 128, 130, 132, 134, 136, 138, 140 may be spaced or configured to hold medium-capacity pill dispensing machines. Additionally or alternatively, the shelves 120, 122 may be configurable to hold capping machines, liquid medicine dispensing machines, pill container storage, cap storage, or other systems used in the fulfillment of prescriptions.

Figure 3A:
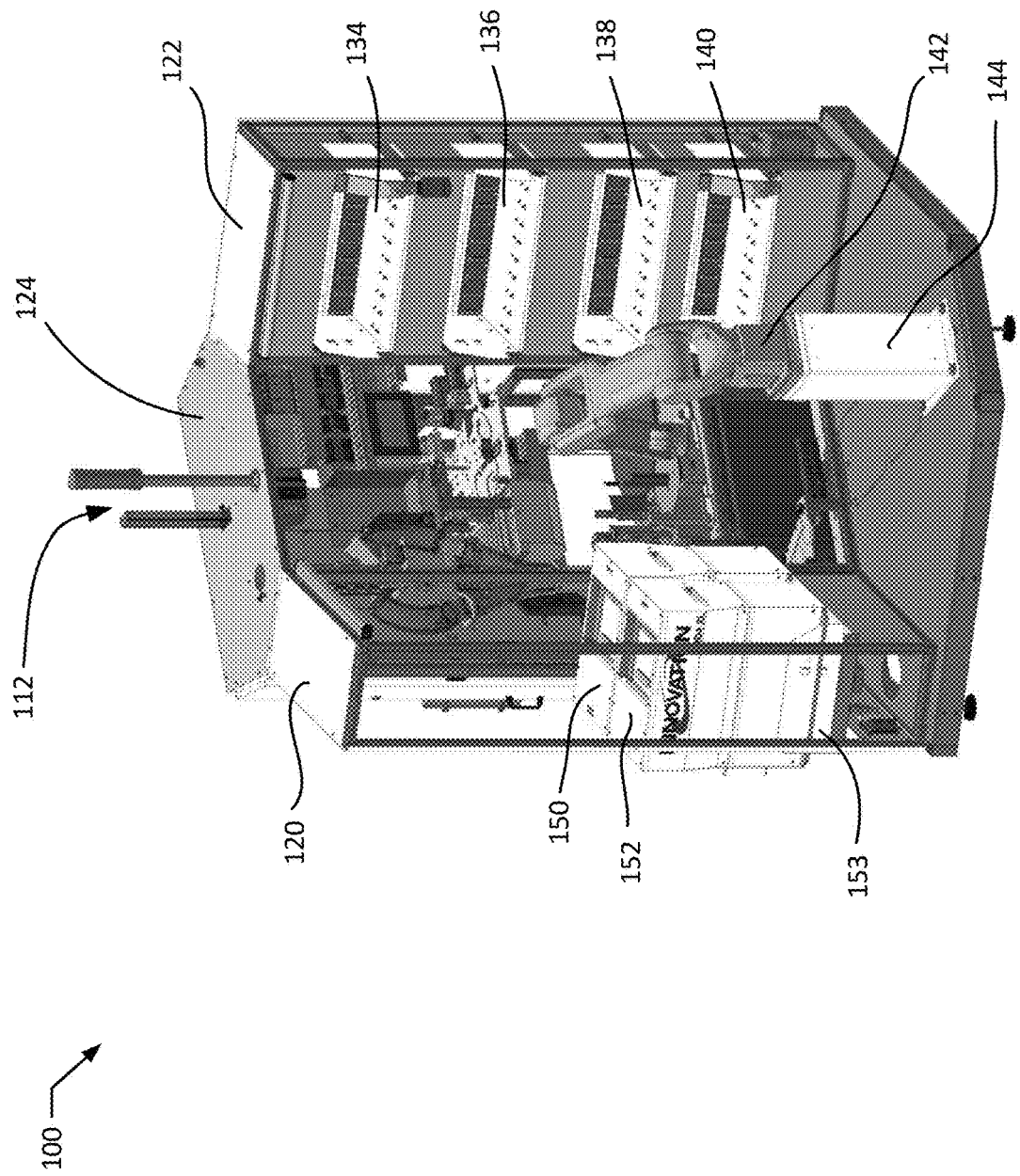
FIG. 3A illustrates an interior view of a prescription filling system in a compact configuration, according to an exemplary embodiment of the present disclosure.

The equipment brackets 126, 128, 130, 132, 134, 136, 138, 140 within the shelves 120, 122 may be replaceable for equipment brackets designed to hold equipment of a different size. For example, FIG. 3A depicts a different configuration of the prescription filling system 100. In particular, in FIG. 3A, the shelf 120 includes an equipment bracket 153 that is configured to store two large pill dispensing machine. As can be seen, the equipment brackets 126, 128, 130 in FIG. 2 may be removed to make room for the large pill dispensing machines 150, 152. In certain instances, the large pill dispensing machines 150, 152 may be securely stored using similar or identical equipment brackets 153 to the equipment brackets 126, 128, 130, 132, 134, 136, 138, 140 used to hold smaller machines. For example, the equipment bracket 153 may be implemented as the equipment bracket 132.

Figure 3B:
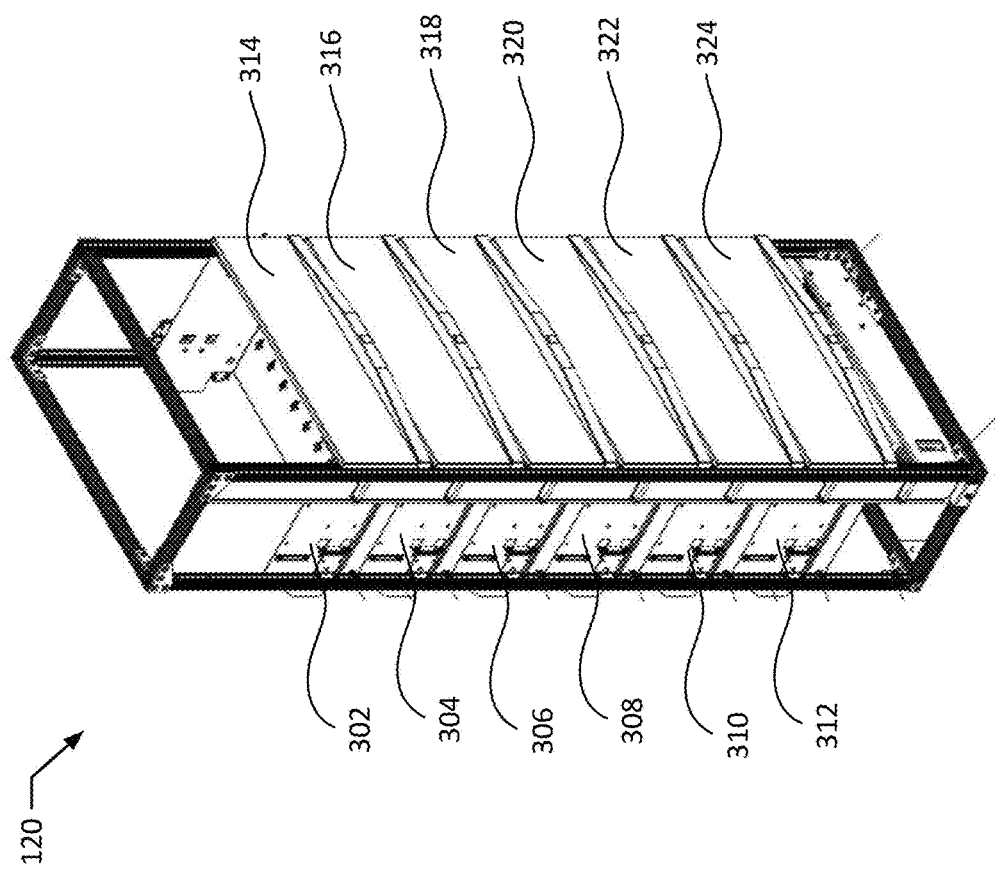
FIG. 3B illustrates a perspective view of a shelf of a prescription filling system, according to an exemplary embodiment of the present disclosure.

As another example, FIG. 3B depicts a different configuration of the shelf 120 that includes six equipment brackets 302, 304, 306, 308, 310, 312. The equipment brackets 302, 304, 306, 308, 310, 312 may be implemented similar to the equipment brackets 126, 128, 130, 132, 134, 136, 153. However, the equipment brackets 302, 304, 306, 308, 310, 312 may be configured to store smaller equipment (e.g., smaller pill dispensing machines, bottle storage systems, cap storage system, and the like). FIG. 3B is shown from the rear of the shelf 120 and depicts back plates 314, 316, 318, 320, 322, 324 of the equipment brackets 302, 304, 306, 308, 310, 312, which may hold stored equipment in position and prevent the equipment from be pushed too far into the equipment brackets 302, 304, 306, 308, 310, 312. Although not separately identified in other figures, the equipment brackets 126, 128, 130, 132, 134, 136, 153 may similarly include back plates. Certain configurations may combine more than one size of equipment bracket. For example, in one instance, a shelf may include a first equipment bracket 153 configured to hold large equipment, a second equipment bracket 128 configured to hold medium-sized equipment, and a third equipment bracket 302 configured to hold small equipment. Any such combination is hereby contemplated within the scope of the present disclosure.

The system 100 also includes a supplementary system 124. The supplementary system 124 may integrate with the ventilation system 112. For example, the supplementary system 124 may include a filtration system that includes a HEPA filtering module that connects to an air intake or an air outlet of the ventilation system 112. In particular, the system 100 may be configured to cooperate with multiple different types of filtration systems and/or filtration systems that integrate with multiple different types of HEPA filters, allowing the particular filtration and/or ventilation performance for the prescription filling system 100 to be customizable on a per application basis (e.g., depending on requirements for the types of medication being dispensed by the prescription filling system 100. The supplementary system 124 may also include a capping system. For example, the capping system may store multiple caps (e.g., for pill containers of different sizes, for different types of caps/threading). Caps may then be retrieved from the capping system and applied to pill containers.

As shown in FIGS. 2 and 3A, the first shelf 120 is connected to a first side of the supplementary system 124. Additionally, the second shelf 122 is connected to a second side, opposite the first side, of the supplementary system 124. In some embodiments, the supplementary system 124 is integrally formed with the first shelf 120 and the second shelf 122.

A robotic arm 142 may be configured to interact with different systems stored within the shelves 120, 122 and/or different systems of the supplementary system 124. For example, the robotic arm 142 may receive a prescription fulfillment request (e.g., via the computer terminal 106). In response, the robotic arm 142 may grab a pill container (e.g., from a pill container storage system located within the supplementary system 124 and/or within one of the equipment brackets 126, 128, 130, 132, 134, 136, 138, 140) and may interact with a pill dispensing machine located on one of the equipment brackets 126, 128, 130, 132, 134, 136, 138, 140 to receive an appropriate number of pills specified within the prescription fulfillment request. Once the pills are received within the pill container, the robotic arm 142 may grab a cap from a capping system and may apply the cap to the top of the pill container, sealing the medication.

The prescription filling system 100 also includes support feet 146, 147, 148. The support feet 146, 147, 148 may be configurable (e.g., adjustable in length) to ensure that the prescription filling system 100 is level during operation. In particular, proper operation of certain types of machines (e.g., pill dispensing machines) may depend on the machines and, by extension, the prescription filling system 100 remaining level while in operation.

Figure 4:
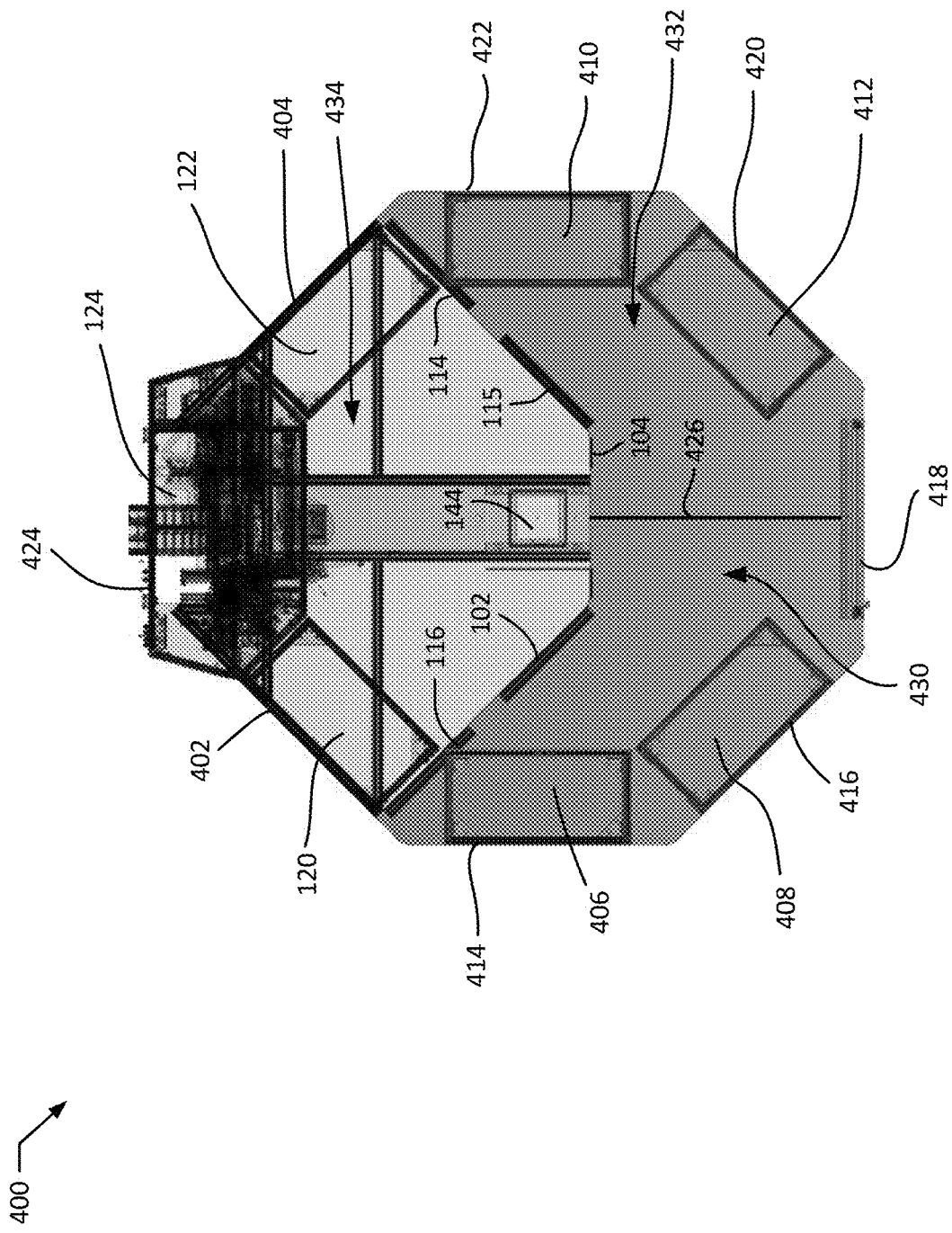
FIG. 4 illustrates an overhead schematic view of a prescription filling system, according to an exemplary embodiment of the present disclosure.

FIG. 4 illustrates an overhead schematic view 400 of the prescription filling systems disclosed herein, according to an exemplary embodiment of the present disclosure. The overhead schematic view 400 depicts an overhead view of the prescription filling system 100, along with additional (darkened) depictions of various expandable configurations for prescription filling systems. As described previously, the compact configuration includes shelves 120, 122, a supplementary system 124, wall portions 104, 114, 115, 116, and a door 102. From the compact configuration, prescription filling systems may be expandable to include additional space for additional equipment. In particular, the prescription filling system may be expandable to a fully expanded configuration with an octagonal shape, as depicted in the overhead schematic view 400. The octagonal shape is formed by the exterior walls 402, 404, 414, 416, 418, 420, 422 and an exterior wall portion of the supplementary system 124. In such an expanded configuration, one or more of the wall portions 104, 114, 115, 116 and the door 102 may be omitted.

In the fully expanded configuration, a prescription filling system may include one or more shelves 406, 408, 410, 412 for at least a subset of the additional exterior walls 414, 416, 420, 422. The prescription filling system may further include a door (e.g., at the external wall 418), which may be used to enter in the prescription filling system, similar to the door 102.

In either configuration, a prescription filling system may include a pedestal 144, which may support a robotic arm 142 used to fulfill prescription requests, as discussed above. In particular, the pedestal 144 may be positioned such that the pedestal 144 is at or near the center of the prescription fulfillment system in the expanded configuration. For example, the pedestal 144 positioned at a similar distance from each of the shelves 120, 122, 406, 408, 410, 412. In a particular example, the pedestal 144 may be positioned such that a robotic arm 142 positioned on the pedestal 144 is able to reach equipment brackets 126, 128, 130, 132, 134, 136, 138, 140 at multiple heights on each of the shelves 120, 122, 406, 408, 410, 412. Notably, in the compact configuration, the pedestal 144 may be positioned such that additional shelves can be added to a prescription fulfillment system (e.g., using additional expansion modules) without having to reposition the pedestal 144 for the robotic arm 142.

Starting from a compact configuration, capacity for a prescription fulfillment system may be expanded on a modular basis. In particular, the fully expanded configuration may comprise three separate modules: a primary module 434 and two expansion modules 430, 432. The primary module 434 may contain the pedestal 144 and may optionally contain a supplementary system 124. In particular, the primary module 434 may include the components of a prescription filling system in a compact configuration, excluding the door 102, wall portions 104, 114, 115, 116, and the computer terminal 106. A first expansion module 430 may include the exterior walls 414, 416 and the shelves 406, 408. A second expansion module 432 may contain the exterior walls 420, 422 and the shelves 410, 412. Expansion modules 430, 432 may be added to a primary module 434 one at a time as needed to gradually expand a prescription fulfillment system. For example, a prescription filling system may be created using the primary module 434 and the first expansion module 430. As another example, a prescription filling system may be created using the primary module 434 and the second expansion module 432. In certain implementations, the expansion modules 430, 432 may be implemented identically (e.g., symmetrically), such that a single expansion module may be used either as the first expansion module 430 or as the second expansion module 432. When only a single expansion module 430, 432 is used, an additional exterior wall 426 may be added to the expansion module 430, 432. The additional exterior wall 426 may include door, similar to the door 102. In certain instances, the door included on the additional exterior wall 426 may be the door 102, repositioned for entry at the additional exterior wall 426. Furthermore, each of the secondary modules 430, 432 may include a portion of the exterior wall 418.

In this way, the modules and associated components (e.g., shelves, equipment brackets) provide for a modularly expandable prescription filling system that can be initially configured at a lower capacity (e.g., using the primary module 434) and can be easily expanded using identical expansion modules as capacity needs increase. Furthermore, within each of the modules, the specific capabilities of the system may be customized for particular deployment needs. In particular, the combination of the shelves and equipment brackets contained therein enable quick adjustment of the specific equipment included within the prescription fulfillment system (e.g., types of machines, capacities of machines, number of machines) accessible via a robotic arm or other fulfillment mechanism of the prescription filling system. In this way, not only can the capacity of the prescription filling system be customized and progressively expanded on a modular basis, but also the capabilities may be expanded and/or custom-tailored as needed. Additionally, by standardizing the hardware that needs to be manufactured for each of the modules 430, 432, 434, modular prescription filling systems such as those described herein may be less expensive to produce, as manufacturing practices and facilities may be standardized.

Figure 5:
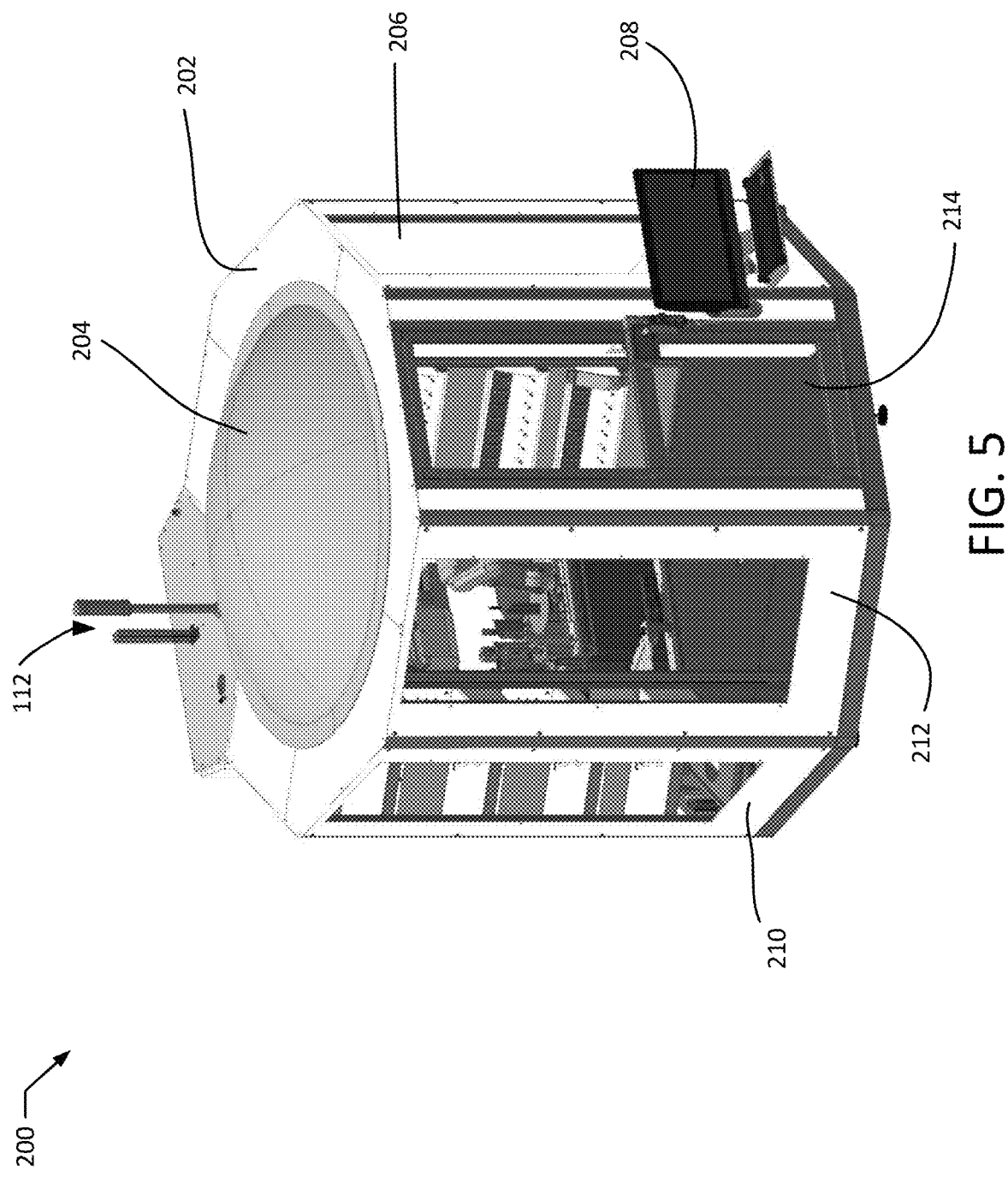
FIG. 5 illustrates an exterior view of a prescription filling system in a fully expanded configuration, according to an exemplary embodiment of the present disclosure.

Turning to FIG. 5, a prescription filling system 200 in a fully expanded configuration is depicted, according to an exemplary embodiment of the present disclosure. The prescription filling system 200 includes wall portions 210, 212, 206. Certain wall portions 210, 212 are transparent and certain wall portions 206 are opaque. The prescription fulfillment system 200 also includes a door 214, which may be similar or identical to the door 102. The prescription filling system 200 also includes a ventilation system 112 and a computer terminal 208, which may be identical to the computer terminal 106. On top, the prescription filling system 200 includes a roof 202 and a convex portion 204. Compared to the convex portion 110, the convex portion 204 is both larger, to cover the greater size of the prescription filling system, and more circular, reflecting the differing proportions between the prescription filling system 100 and the prescription filling system 200.

In certain instances, the prescription filling system 200 may be created by adding expansion modules, such as the expansion modules 430, 432, to the prescription filling system 100. For example, the wall portions 104 and the door 102 may be removed from the prescription filling system 100, along with the convex portion 110 of the roof 108. Expansion modules may then be added to the prescription filling system 100, along with additional wall portions to connect the prescription filling system 100 to each of the expansion modules. In certain implementations, one or more of the wall portion 104 and the door 102 may be reused. For example, the door 102 may be installed as the door 214 in a fully expanded prescription filling system 200. As another example, a transparent wall portion may be used as the wall portion 212. In this way, as explained above, expansion modules may be used to transition between prescription filling systems 100 in compact configurations and prescription filling systems 200 in expanded configurations as needed.

It should be understood that various changes and modifications to the examples described here will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A prescription filling system comprising:
    a primary module comprising:
        a perimeter that includes three walls adjacent to each other and three removable wall portions including a middle removable wall portion located between two side removable wall portions, the middle removable wall portion having a length that is less than lengths of the two side removable wall portions,
        a first shelf containing a first plurality of equipment brackets,
        a second shelf containing a second plurality of equipment brackets,
        a supplementary system positioned between the first shelf and the second shelf, and
        a robotic arm,
        wherein the first shelf is located at a first wall of the primary module, the supplementary system is located at a second wall adjacent to the first wall of the primary module, the second shelf is located at a third wall adjacent to the second wall of the primary module, and the robotic arm is adjacent to the middle removable wall portion of the primary module; and
    at least one expansion module removably connected to the primary module, the at least one expansion module comprising:
        a first exterior wall configured to connect to the first wall of the primary module,
        a second exterior wall configured to connect to the second wall of the primary module, and
        three exterior walls connected between the first and second exterior walls,
        a third shelf containing a third plurality of equipment brackets located at the first exterior wall, and
        a fourth shelf containing a fourth plurality of equipment brackets located at the second exterior wall,
    wherein the robotic arm is substantially equidistant from each of the first shelf, the second shelf, the third shelf, and the fourth shelf when the at least one expansion module is connected to the primary module, and
    wherein the three removable wall portions are disconnected from the primary module when the at least one expansion module is connected to the primary module.

2. The system of claim 1, wherein the first shelf is connected to a first side of the supplementary system and the second shelf is connected to a second side, opposite the first side, of the supplementary system.

3. The system of claim 1, wherein at least one of the first shelf, the second shelf, the third shelf, or the fourth shelf includes a first equipment bracket configured to hold large equipment and at least one of a second equipment bracket configured to hold medium-sized equipment or a third equipment bracket configured to hold small equipment.

4. The system of claim 1, wherein at least one of the first shelf, the second shelf, the third shelf, or the fourth shelf includes between two and seven equipment brackets.

5. The system of claim 1, wherein at least one of the first plurality of equipment brackets, the second plurality of equipment brackets, the third plurality of equipment brackets, or the fourth plurality of equipment brackets are replaceable with other-sized equipment brackets.

6. The system of claim 1, wherein at least one of the first plurality of equipment brackets, the second plurality of equipment brackets, the third plurality of equipment brackets, or the fourth plurality of equipment brackets are configured to hold at least one of pill dispensing machines, capping machines, liquid medicine dispensing machines, pill container storage, or cap storage.

7. The system of claim 1, wherein the supplementary system includes a filtration system that contains a HEPA filtering module.

8. The system of claim 1, wherein the robotic arm is positioned in a fixed location on the primary module to be substantially equidistant from each of the first shelf, the second shelf, the third shelf, and the fourth shelf when the at least one expansion module is connected to the primary module.

9. The system of claim 1, wherein the at least one expansion module includes two expansion modules that are connected to the primary module.

10. The system of claim 1, wherein the at least one expansion module includes two expansion modules, and wherein the primary module and the two expansion modules form an octagon shape when viewed from overhead.

11. The system of claim 10, wherein the robotic arm is positioned in a center of the octagon.

12. The system of claim 10, wherein the two expansion modules each comprises two sides of the octagon and connect together to form another side of the octagon.

13. The system of claim 12, wherein the primary module includes three sides of the octagon and is connected to a side of each of the expansion modules.

14. The system of claim 12, wherein the primary module includes a pedestal upon which the robotic arm is placed.

15. The system of claim 12, wherein the walls of the primary module and the exterior walls of the two expansion modules are positioned at the sides of the octagon.

16. The system of claim 15, wherein the walls of the primary module and the exterior walls of the two expansion modules are connected to a roof to form a sealed environment.

17. A method of assembling a prescription filling system, comprising:
   providing a primary module, the primary module comprising:
      a perimeter that includes three walls adjacent to each other and three removable wall portions including a middle removable wall portion located between two side removable wall portions, the middle removable wall portion having a length that is less than lengths of the two side removable wall portions,
      a first shelf containing a first plurality of equipment brackets,
      a second shelf containing a second plurality of equipment brackets,
      a supplementary system positioned between the first shelf and the second shelf, and
      a robotic arm,
      wherein the first shelf is located at a first wall of the primary module, the supplementary system is located at a second wall adjacent to the first wall of the primary module, the second shelf is located at a third wall adjacent to the second wall of the primary module, and the robotic arm is adjacent to the middle removable wall portion of the primary module; and
   providing at least one expansion module, the expansion module comprising:
      a first exterior wall configured to connect to the first wall of the primary module,
      a second exterior wall configured to connect to the second wall of the primary module, and
      three exterior walls connected between the first and second exterior walls,
      a third shelf containing a third plurality of equipment brackets located at the first exterior wall, and
      a fourth shelf containing a fourth plurality of equipment brackets located at the second exterior wall;
   removing the removable wall by disconnecting the three removable wall portions from the primary module; and
   attaching the at least one expansion module to the primary module,
   wherein the robotic arm is substantially equidistant from each of the first shelf, the second shelf, the third shelf, and the fourth shelf when the at least one expansion module is attached to the primary module.

18. The method of claim 17, wherein the attachment of the at least one expansion module to the primary module is made without having to re-position the robotic arm.

19. The method of claim 17, wherein at least one of the first plurality of equipment brackets, the second plurality of equipment brackets, the third plurality of equipment brackets, or the fourth plurality of equipment brackets are configured to hold at least one of pill dispensing machines, capping machines, liquid medicine dispensing machines, pill container storage, or cap storage.

* * * * *